United States Patent [19]
Anderegg

[11] Patent Number: 4,960,112
[45] Date of Patent: Oct. 2, 1990

[54] BREAST BINDER FOR SUPPRESSION OF POSTPARTUM LACTATION

[76] Inventor: Linda S. Anderegg, 5236 S. Melvina, Chicago, Ill. 60638

[21] Appl. No.: 396,039

[22] Filed: Aug. 21, 1989

[51] Int. Cl.$^5$ ............ A61F 5/02; A61F 5/04; A41B 1/18
[52] U.S. Cl. ............ 128/78; 128/87 R; 2/118
[58] Field of Search ............ 128/889, DIG. 20, 87 R, 128/155, 156, 78, 75; 2/118

[56] References Cited

U.S. PATENT DOCUMENTS

| | | | |
|---|---|---|---|
| 2,450,298 | 9/1948 | Peterson | 128/87 R |
| 2,505,720 | 4/1950 | Peiser | 128/889 |
| 3,115,879 | 12/1963 | Kaplan | 128/165 |
| 3,499,441 | 3/1970 | Hall | 128/87 R |
| 3,521,623 | 7/1970 | Nichols | 128/87 R |
| 3,561,436 | 2/1971 | Gaylord, Jr. | 128/87 R |
| 3,752,163 | 8/1973 | Kaplan | 450/117 |
| 3,902,503 | 9/1975 | Gaylord, Jr. | 128/165 |
| 3,921,222 | 11/1975 | Hollman | 128/78 |
| 3,926,183 | 12/1975 | Spiro | 128/78 |
| 3,970,079 | 7/1976 | Gaylord, Jr. | 128/78 |
| 4,120,297 | 10/1978 | Rabischong | 128/DIG. 20 |
| 4,245,628 | 1/1981 | Eichler | 128/78 |
| 4,269,179 | 5/1981 | Burton | 128/78 |
| 4,572,167 | 2/1986 | Brunswick | 128/78 |

Primary Examiner—Robert A. Hafer
Assistant Examiner—Michael Brown
Attorney, Agent, or Firm—Mathew L. Kalinowski

[57] ABSTRACT

A breast binder for the suppression of postpartum lactation and for relieving the discomfort of breast engorgement includes a double layer of cloth panels joined end to end in torso encircling configuration; a plurality of releasable and adjustable fastening means disposed vertically along the ends of the binder, each of which can be independently adjusted to provide the compression to the breasts required to suppress lactation; and, shoulder straps having individually adjustable fastening means to optimize uplift support to the breasts to relieve the discomfort of breast engorgement.

6 Claims, 1 Drawing Sheet

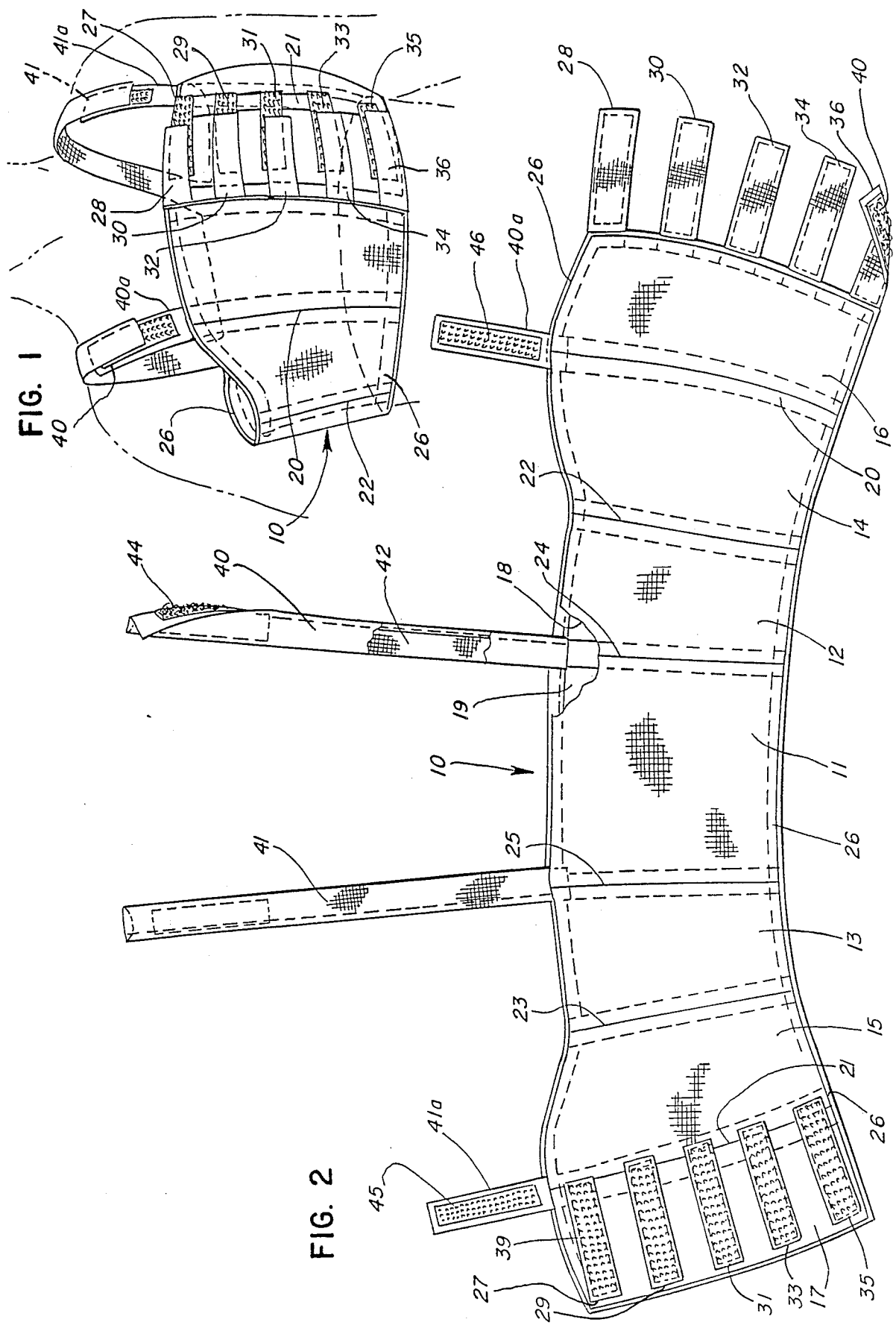

BREAST BINDER FOR SUPPRESSION OF POSTPARTUM LACTATION

This invention relates to a breast binder for the suppression of postpartum lactation. Additionally, this invention relates to a breast binder that offers supportive therapy to minimize the discomfort of mammary congestion and engorgement.

Suppression of postpartum lactation is practiced when the mother elects not to breast feed, when breast feeding is contraindicated for medical reasons, or after stillbirth, neonatal death, or adoption. Lactation can be suppressed by medicinal or by mechanical means. Medicinal therapy involves the administration of hormones, such as the estrogens, or prolactin inhibiting drugs, such as the bromocriptines. Such therapy is effective but in the case of estrogen usage poses the serious risk of endometrial cancer or thromboembolism. In the case of bromocriptine usage, the most frequent undesirable side-effects are hypotension, headache, dizziness, nausea, vomiting, and fatigue. Both types of drugs can induce myocardial infarction and stroke.

Mechanical suppression of lactation is generally free of the above-cited disadvantages of medicinal therapy. In its elementary form, tight compression is applied to the breasts by means of strips of toweling or other suitable cloth wrapped and fastened about the upper torso. The wrapping is worn until lactation ceases which usually occurs in from about a week to about a month.

The prior art discloses a variety of body support garments and binders. For example, Kaplan, U.S. Pat. No. 3,115,879 discloses a binder, primarily for abdominal support, that comprises a plurality of parallel panels of elastic webbing stretchable in the body-encircling direction. The parallel panels are arranged vertically so as to aid in holding the binder in place. An improvement on this binder is taught in Kaplan, U.S. Pat. No. 3,752,163 wherein the binder incorporates an adjustable panel that enables the binder to be used over a range of sizes. Gaylord, U.S. Pat. No. 3,902,503 discloses a surgical binder comprising vertically arranged panels that encircle the body. A removable panel is incorporated in the binder to permit use over a range of sizes. Gaylord, U.S. Pat. No. 3,970,079 discloses a binder comprising panels joined by rigid plastic strips to resist rolling of the edges of the binder when in use. The prior art binders cited above are poorly suited for the suppression of lactation. For example, close conformation to the shape of the breast is lacking as well as means for providing adjustable compression and uplift support to the breasts, features that are critical for effective suppression of lactation and for comfort in wear.

Accordingly, it is an object of this invention to provide a breast binder for suppression of postpartum lactation that conforms closely to the shape of the breasts and that provides a plurality of releasable and adjustable fastening means for applying compression to the breasts.

It is a further object of this invention to provide a breast binder that supplies uplift support to prevent post-partum stretching and breakdown of breast tissues and to minimize congestion, engorgement, and discomfort, and to inhibit the let-down reflex.

These and other objects will become apparent as description of the invention proceeds.

The breast binder of this invention, adapted to encircle the upper torso of a wearer, comprises a first binder section having a plurality of cloth panels joined end to end by means of flat seams, the panels covering the breasts being of breast-conforming configuration; a second binder section essentially identical to the first section and joined to it to form a two-layered breast binder; a plurality of fastening means vertically disposed at the ends of the two-layered binder for releasably and adjustably connecting the ends of the binder to apply compression to the breasts; and shoulder straps secured to the top edge of the binder having releasable and adjustable fastening means to provide uplift support to the breasts.

The vertically arranged fastening means at the ends of the binder enable the wearer to adjust each fastener individually to provide the optimum conformation to and compression of the breasts for suppression of lactation. The shoulder straps with adjustable fastening means provide the uplift support required to minimize stretching and breakdown of breast tissues and the discomfort of breast engorgement and congestion. The configuration of the binder together with the arrangement of fastening means provide a binder that the wearer can easily put in place without assistance.

The panels of the binder can be fabricated from conventional textile fabrics. Preferred fabrics are non-stretchable, absorbent, and washable, for example, muslin cloth and similar cotton-containing materials. A variety of fastening means can be employed, such as interconnecting straps and eyelets, lacing arrangements, and the like. Particularly suitable and preferred fastening means comprise strips of Velcro-type fasteners which utilize male hook-shaped fibrous members that releasably and adustably engage female fibrous members in an overlapping arrangement.

BRIEF DESCRIPTION OF THE DRAWINGS

FIG. 1 is a front elevation view of the breast binder of this invention in place about the upper torso.

FIG. 2 is a plan view of the binder.

DESCRIPTION OF THE PREFERRED EMBODIMENT

The invention is further illustrated by reference to the drawings wherein like reference numerals designate identical or corresponding parts throughout the two figures.

In FIG. 2 breast binder 10 comprises a center back panel 11 adjoining side back panels 12 and 13, which adjoin side front panels 14 and 15, which in turn adjoin center front panels 16 and 17 to form first body-encircling section 18. The panels of section 18 are joined by the flat seams shown at 20, 21, 22, 23, 24, and 25 (seam allowance is represented at each seam by broken lines). A second binder section 19 is fabricated in a configuration identical to that of section 18. The two sections are joined by seam 26, shown along the entire periphery of the joined sections, to form the two-layered binder 10.

Fastening means 28, 30, 32, 34, and 36 are vertically disposed along the edge of panel 16 to provide closure at the front of binder 10 by engaging fastening means 27, 29, 31, 33, and 35 secured to panel 17. Preferably, loose fibrous female strips 40 are secured to each of fasteners 28, 30, 32, 34, and 36, and male hook-shaped fibrous members 39 are secured to each of fasteners 27, 29, 31, 33, and 35. The plurality of fastening means arranged vertically along the edges of panels 16 and 17 provide for releasable and adjustable closure of binder 10.

Shoulder strap 40 is joined to the top of binder 10 at the juncture of panels 11 and 12; shoulder strap 40a is joined to the top of binder 10 at the juncture of panels 14 and 16 and, in use, engages strap 40. Similarly, shoulder strap 41 is joined to the top edge of binder 10 at the juncture of panels 11 and 13, and shoulder strap 41a is joined at the top of binder 10 at the juncture of panels 15 and 17. Each of the shoulder straps is fabricated of a double layer of material as is shown at cutaway 42. Female Velcro-type fastening means as shown at 44 are provided at straps 40 and 41 which engage male Velcro-type fastening means 46 and 45 at straps 40a and 41a.

FIG. 1 shows binder 10 in place about the upper torso. It is clear that each of the vertically arranged fastener pairs 27-28, 29-30, 31-32, 33-34, and 35-36 can be adjusted independently to provide a binding force in the horizontal direction. Such individual adjustment enables the wearer to conform the front panels of the binder closely to the shape of the breasts and to provide the required compression of the breasts for effective suppression of lactation. It is also clear that each shoulder strap can be individually adjusted to optimize the uplift support required to aid in the suppression of lactation and to minimize the discomfort of breast engorgement and congestion.

Three newly-delivered women, Volunteers A, B, and C, who had normal deliveries and healthy infants, participated in an evaluation of the breast binder of this invention. A fourth woman, Volunteer D, used the binder after breast feeding for a period of five months.

Volunteer A began applying and adjusting the binder three days after delivery when the breasts began filling with milk; engorgement of the breasts was unusually high. Discomfort was relieved after three days and lactation ceased after three days. No rebound lactation occurred.

Volunteer B began applying and adjusting the binder two days after delivery when the breasts began filling with milk and became engorged. After five days, wearing of the binder was discontinued at which time discomfort of engorgement was relieved. A small leakage of milk persisted but eventually ceased entirely at the end of two weeks. No rebound lactation occurred.

Volunteer C began applying and adjusting the binder two days after delivery when the breasts began filling with milk and became engorged. The binder was worn four days after which engorgement was relieved. The milk supply which initially was very large was reduced to a small amount after four days and ceased entirely after thirteen days. No rebound lactation was observed.

Volunteer D after five months of breast feeding began using the binder to relieve engorgement during the transition from breast to bottle feeding. Discomfort was relieved after twelve days and lactation ceased after fifteen days.

The results of the evaluation program above indicate that newly-delivered women can easily and effectively utilize the breast binder of this invention to suppress postpartum lactation and to relieve the discomfort of engorgement. The results further indicate that the binder is also effective when suppression of lactation and relief from engorgement are desired after a period of breast feeding.

Although this invention has been described with particular reference to certain preferred embodiments thereof, it is understood that variations and modifications can be effected within the scope and spirit of the appended claims. It is intended that all matter contained in the above description and figures shall be interpreted in an illustrative and not in a limiting sense.

What is claimed is:

1. A breast binder adapted to encircle the upper torso of a wearer and apply releasable and adjustable compression and uplift to the breasts, said binder comprising:
   a first binder section having a plurality of non-stretchable cloth panels each said panel joined end to end with adjacent panels to form a continuous section of length sufficient to encircle the upper torso;
   a second binder section essentially identical in construction and form to the first section and being joined to it in an overlapping arrangement to form a two-layered binder;
   a plurality of releasable and independently adjustable fastening means vertically disposed along the ends of the two-layered binder for applying breast-conforming compression to the breasts sufficient to cause cessation of lactation; and
   shoulder straps attached to the top edge of the two-layered binder and having releasable and adjustable fastening means to provide uplift support to the breasts sufficient to relieve the discomfort of breast engorgement.

2. The breast binder of claim 1 wherein the cloth panels are of, absorbent textile fabric.

3. The breast binder of claim 1 wherein the cloth panels are of non-stretchable muslin fabric.

4. The breast binder of claim 1 wherein the cloth panels and binder sections are joined by means of stitched seams.

5. The breast binder of claim 1 wherein each of the fastening means vertically disposed along one end of the binder comprise strips of male, hook-shaped fibrous members, and each of the opposing fastening means vertically disposed along the other end of the binder comprise female, loose fibrous members, overlapping joining of opposing male and female strips providing releasable and adjustable closure of the ends of the binder.

6. The breast binder of claim 1 wherein the fastening means of the shoulder straps comprise strips of female, loose fibrous members attached to the ends of the shoulder straps and strips of male, hook-shaped fibrous members attached to the top edge of the binder, overlapping joining of male and female strips providing releasable and adjustable fastening of the shoulder straps.

* * * * *